US 11,590,873 B2

(12) United States Patent
Migneco et al.

(10) Patent No.: US 11,590,873 B2
(45) Date of Patent: Feb. 28, 2023

(54) SEAT ASSEMBLY

(71) Applicant: Lear Corporation, Southfield, MI (US)

(72) Inventors: Francesco Migneco, Saline, MI (US); David Gallagher, Sterling Heights, MI (US)

(73) Assignee: Lear Corporation, Southfield, MI (US)

( * ) Notice: Subject to any disclaimer, the term of this patent is extended or adjusted under 35 U.S.C. 154(b) by 0 days.

(21) Appl. No.: 15/930,777

(22) Filed: May 13, 2020

(65) Prior Publication Data

US 2021/0354612 A1    Nov. 18, 2021

(51) Int. Cl.
*B60N 2/90* (2018.01)
*A61B 5/0205* (2006.01)
*B60N 2/885* (2018.01)
*B60N 2/02* (2006.01)

(52) U.S. Cl.
CPC ............ *B60N 2/976* (2018.02); *A61B 5/0205* (2013.01); *B60N 2/914* (2018.02); *B60N 2/99* (2018.02); *B60N 2/0296* (2013.01); *B60N 2/885* (2018.02)

(58) Field of Classification Search
CPC ........... B60N 2/976; B60N 2/99; B60N 2/914
See application file for complete search history.

(56) References Cited

U.S. PATENT DOCUMENTS

| 5,769,490 A | 6/1998 | Falzon |
|---|---|---|
| 6,056,360 A | 5/2000 | Schneider |
| 6,079,485 A | 6/2000 | Esaki et al. |
| 6,088,642 A | 7/2000 | Finkelstein et al. |
| 6,088,643 A | 7/2000 | Long et al. |
| 6,098,000 A | 8/2000 | Long et al. |
| 6,179,378 B1 | 1/2001 | Baumgartner et al. |
| 6,345,839 B1 | 2/2002 | Kuboki et al. |
| 6,353,207 B1 | 3/2002 | Burt |
| 6,506,153 B1 | 1/2003 | Littek et al. |
| 6,559,422 B2 | 5/2003 | Burt |
| 6,682,494 B1 | 1/2004 | Sleichter, III et al. |
| 6,908,152 B2 | 6/2005 | McMillen |
| 7,011,369 B2 | 3/2006 | Massara et al. |
| 7,083,232 B2 | 8/2006 | Frank |
| 7,083,233 B2 | 8/2006 | Massara et al. |
| 7,152,920 B2 | 12/2006 | Sugiyama et al. |

(Continued)

FOREIGN PATENT DOCUMENTS

| CN | 2855822 Y | 1/2007 |
|---|---|---|
| CN | 2012065729 A | 4/2012 |

(Continued)

OTHER PUBLICATIONS

Co-Pending U.S. Appl. No. 16/821,128, filed Mar. 17, 2020.

(Continued)

*Primary Examiner* — Timothy J Brindley
(74) *Attorney, Agent, or Firm* — Fishman Stewart PLLC

(57) ABSTRACT

A seat assembly may include a seat, a first bladder assembly connected to the seat, a second bladder assembly connected to the seat, and/or an electrical control unit (ECU) configured to independently control the first bladder assembly and the second bladder assembly. The ECU may be configured to maintain a level of inflation of the first bladder assembly to provide a hugging effect to a user of the seat while inflating and deflating the second bladder assembly to guide breathing of said user.

18 Claims, 5 Drawing Sheets

(56) References Cited

U.S. PATENT DOCUMENTS

| | | | |
|---|---|---|---|
| 7,201,446 B2 | 4/2007 | Massara et al. | |
| 7,219,923 B2 | 5/2007 | Fujita et al. | |
| 7,267,652 B2 | 9/2007 | Coyle et al. | |
| 7,303,231 B2 | 12/2007 | Frank | |
| 7,314,451 B2 | 1/2008 | Halperin et al. | |
| 7,417,536 B2 | 8/2008 | Lakshmanan et al. | |
| 7,688,582 B2 | 3/2010 | Fukazu et al. | |
| 7,731,279 B2 | 6/2010 | Asada et al. | |
| 7,808,395 B2 | 10/2010 | Raisanen et al. | |
| 7,828,050 B2 | 11/2010 | Esaki | |
| 7,862,119 B2 | 1/2011 | Schafer et al. | |
| 7,866,755 B2 | 1/2011 | Okano | |
| 7,900,736 B2 | 3/2011 | Breed | |
| 7,967,379 B2 | 6/2011 | Walters et al. | |
| 7,967,381 B2 | 6/2011 | Sugiyama | |
| 8,341,786 B2 | 1/2013 | Oexman et al. | |
| 8,444,558 B2 | 5/2013 | Young et al. | |
| 8,616,654 B2 | 12/2013 | Zenk et al. | |
| 8,618,451 B2 | 12/2013 | Kunisada | |
| 8,706,204 B2 | 4/2014 | Seo et al. | |
| 8,710,784 B2 | 4/2014 | Meyer et al. | |
| 8,725,311 B1 | 5/2014 | Breed | |
| 8,794,707 B2 | 8/2014 | Bocsanyi et al. | |
| 8,827,372 B2 | 9/2014 | Yoon | |
| 8,958,955 B2 | 2/2015 | Hotary et al. | |
| 8,971,839 B2 | 3/2015 | Hong | |
| 8,979,191 B2 | 3/2015 | Friderich et al. | |
| 8,989,697 B2 | 3/2015 | Leung et al. | |
| 9,147,192 B2 | 9/2015 | Dawson et al. | |
| 9,237,242 B2 | 1/2016 | Basir | |
| 9,272,647 B2 | 3/2016 | Gawade et al. | |
| 9,272,689 B2 | 3/2016 | Fung et al. | |
| 9,277,385 B2 | 3/2016 | Iwamoto | |
| 9,504,416 B2 | 11/2016 | Young et al. | |
| 9,815,385 B2 | 11/2017 | Lippman et al. | |
| 9,848,814 B2 | 12/2017 | Benson et al. | |
| 9,883,821 B2 | 2/2018 | Muehlsteff | |
| 9,978,283 B2 | 5/2018 | Jedrzejewski et al. | |
| 9,980,680 B2 | 5/2018 | Matsumoto | |
| 10,034,631 B1 | 7/2018 | Gallagher et al. | |
| 10,210,409 B1 | 2/2019 | Migneco et al. | |
| 10,213,147 B2 | 2/2019 | Gallagher et al. | |
| 10,220,756 B2 | 3/2019 | Onuma | |
| 10,308,258 B2 | 6/2019 | Fung et al. | |
| 10,328,823 B2 | 6/2019 | O'Bannon et al. | |
| 10,358,065 B2 | 7/2019 | McMillen et al. | |
| 10,369,074 B2 | 8/2019 | Oberg et al. | |
| 10,379,535 B2 | 8/2019 | Migneco et al. | |
| 10,391,900 B2 | 8/2019 | Zhao et al. | |
| 10,470,968 B2 | 11/2019 | Saren et al. | |
| 10,471,868 B2 | 11/2019 | Wheeler | |
| 10,492,979 B2 | 12/2019 | Norman et al. | |
| 10,556,532 B2 | 2/2020 | Gallagher et al. | |
| 10,562,412 B1 | 2/2020 | Main et al. | |
| 10,569,668 B2 | 2/2020 | Migneco et al. | |
| 10,576,855 B2 | 3/2020 | Dorfler et al. | |
| 10,640,010 B2 | 5/2020 | Yetukur et al. | |
| 10,709,386 B2 | 7/2020 | Gallagher et al. | |
| 10,744,920 B2 | 8/2020 | Strumolo | |
| 10,807,439 B2 | 10/2020 | Migneco et al. | |
| 10,898,708 B2 | 1/2021 | Franco-Obregon et al. | |
| 11,059,490 B1* | 7/2021 | Migneco .............. | A61B 5/6893 |
| 2003/0039298 A1 | 2/2003 | Eriksson et al. | |
| 2003/0075959 A1 | 4/2003 | Xue et al. | |
| 2003/0209893 A1 | 11/2003 | Breed et al. | |
| 2004/0119599 A1 | 6/2004 | Stevenson et al. | |
| 2004/0129478 A1 | 7/2004 | Breed et al. | |
| 2006/0244289 A1 | 11/2006 | Bedro | |
| 2007/0118054 A1 | 5/2007 | Pinhas et al. | |
| 2008/0161989 A1 | 7/2008 | Breed | |
| 2008/0216567 A1 | 9/2008 | Breed | |
| 2008/0255731 A1 | 10/2008 | Mita et al. | |
| 2008/0267460 A1 | 10/2008 | Aoki et al. | |
| 2008/0288406 A1 | 11/2008 | Seguin et al. | |
| 2009/0008970 A1 | 1/2009 | Flory et al. | |
| 2009/0030578 A1 | 1/2009 | Periot et al. | |
| 2010/0087748 A1 | 4/2010 | Tobola et al. | |
| 2011/0015468 A1 | 1/2011 | Aarts et al. | |
| 2012/0080911 A1 | 4/2012 | Brykalski et al. | |
| 2012/0086249 A1 | 4/2012 | Hotary et al. | |
| 2012/0089299 A1 | 4/2012 | Breed | |
| 2012/0116149 A1 | 5/2012 | Pilla et al. | |
| 2013/0090816 A1 | 4/2013 | Huber | |
| 2013/0127210 A1 | 5/2013 | Jung et al. | |
| 2013/0251216 A1 | 9/2013 | Smowton et al. | |
| 2014/0070943 A1 | 3/2014 | Breed | |
| 2014/0132042 A1 | 5/2014 | Midderhoff et al. | |
| 2014/0207333 A1 | 7/2014 | Vandivier et al. | |
| 2014/0319895 A1 | 10/2014 | Lange-Mao et al. | |
| 2014/0361871 A1 | 12/2014 | Silva et al. | |
| 2014/0375089 A1 | 12/2014 | Qureshi et al. | |
| 2015/0048658 A1 | 2/2015 | Gawade et al. | |
| 2015/0084985 A1 | 3/2015 | Baudu | |
| 2015/0126916 A1* | 5/2015 | Hall .................. | B60N 2/42 |
| | | | 601/149 |
| 2015/0266405 A1 | 9/2015 | Fitzpatrick et al. | |
| 2015/0313475 A1 | 11/2015 | Benson et al. | |
| 2015/0351692 A1 | 12/2015 | Pereny et al. | |
| 2015/0352979 A1 | 12/2015 | O'Bannon et al. | |
| 2015/0352990 A1 | 12/2015 | Zouzal et al. | |
| 2015/0375653 A1 | 12/2015 | Josefsson et al. | |
| 2016/0001781 A1 | 1/2016 | Fung et al. | |
| 2016/0003882 A1 | 1/2016 | Loftus | |
| 2016/0129920 A1 | 5/2016 | Hall et al. | |
| 2016/0143803 A1 | 5/2016 | Portales | |
| 2016/0176409 A1 | 6/2016 | Kirsch et al. | |
| 2016/0250956 A1 | 9/2016 | Seiting et al. | |
| 2016/0278709 A1 | 9/2016 | Ridao Granado et al. | |
| 2017/0043681 A1 | 2/2017 | Seiller et al. | |
| 2017/0086588 A1 | 3/2017 | Patrick et al. | |
| 2017/0225591 A1 | 8/2017 | Tobata et al. | |
| 2017/0274906 A1 | 9/2017 | Hassan et al. | |
| 2017/0349061 A1 | 12/2017 | Benson et al. | |
| 2017/0361748 A1 | 12/2017 | Meachum et al. | |
| 2018/0008507 A1 | 1/2018 | Saren et al. | |
| 2018/0009343 A1 | 1/2018 | Saren et al. | |
| 2018/0015853 A1* | 1/2018 | Lem .................. | B60N 2/0244 |
| 2018/0065642 A1 | 3/2018 | Frye et al. | |
| 2018/0110960 A1 | 4/2018 | Youngblood et al. | |
| 2018/0178692 A1 | 6/2018 | Zhao et al. | |
| 2018/0178808 A1 | 6/2018 | Zhao et al. | |
| 2018/0215293 A1 | 8/2018 | Gandhi et al. | |
| 2018/0325264 A1 | 11/2018 | Gallagher et al. | |
| 2018/0345833 A1 | 12/2018 | Gallagher et al. | |
| 2018/0361897 A1* | 12/2018 | Lem .................. | B60N 2/646 |
| 2019/0053761 A1 | 2/2019 | Young et al. | |
| 2019/0054796 A1 | 2/2019 | Thomas | |
| 2019/0121356 A1* | 4/2019 | Migneco ............. | A61B 5/746 |
| 2019/0126036 A1 | 5/2019 | Franco-Obregon et al. | |
| 2019/0133511 A1* | 5/2019 | Migneco ............. | A61B 5/0077 |
| 2019/0168771 A1 | 6/2019 | Migneco et al. | |
| 2019/0193591 A1 | 6/2019 | Migneco et al. | |
| 2019/0239815 A1 | 8/2019 | Gallagher et al. | |
| 2019/0275860 A1 | 9/2019 | Migneco et al. | |
| 2019/0332902 A1 | 10/2019 | Gallagher et al. | |
| 2019/0337412 A1 | 11/2019 | Zouzal et al. | |
| 2019/0337431 A1 | 11/2019 | McMillen et al. | |
| 2019/0344043 A1* | 11/2019 | Migneco ............. | B60N 2/0244 |
| 2020/0035237 A1 | 1/2020 | Kim et al. | |
| 2020/0113344 A1 | 4/2020 | Youngblood et al. | |
| 2020/0170576 A1 | 6/2020 | Lerner | |
| 2020/0188211 A1 | 6/2020 | Ellermann | |
| 2020/0231428 A1 | 7/2020 | Migneco et al. | |
| 2020/0253381 A1 | 8/2020 | Dorfler et al. | |
| 2020/0324675 A1 | 10/2020 | Yamamoto et al. | |
| 2021/0016686 A1 | 1/2021 | Yetukuri et al. | |

FOREIGN PATENT DOCUMENTS

| | | |
|---|---|---|
| CN | 203186154 U | 9/2013 |
| CN | 203611819 U | 5/2014 |
| CN | 104252615 A | 12/2014 |
| CN | 105799566 A | 7/2016 |
| CN | 205468657 U | 8/2016 |

(56) References Cited

FOREIGN PATENT DOCUMENTS

| | | |
|---|---|---|
| CN | 106068097 A | 11/2016 |
| CN | 107826010 A | 3/2018 |
| CN | 108297771 A | 7/2018 |
| DE | 10027686 A1 | 1/2002 |
| DE | 10063478 A1 | 7/2002 |
| DE | 102004010626 A1 | 6/2005 |
| DE | 102004013674 A1 | 10/2005 |
| DE | 102006029871 A1 | 1/2008 |
| DE | 102008029339 A1 | 1/2009 |
| DE | 102009008421 A1 | 10/2009 |
| DE | 102009035566 A1 | 2/2010 |
| DE | 102009031331 A1 | 8/2010 |
| DE | 102009033041 A1 | 1/2011 |
| DE | 102010021332 A1 | 1/2011 |
| DE | 102007006866 B4 | 11/2011 |
| DE | 102010049152 A1 | 11/2011 |
| DE | 102011012431 A1 | 11/2011 |
| DE | 102011016073 A1 | 12/2011 |
| DE | 102011017238 A1 | 12/2011 |
| DE | 102011102021 A1 | 11/2012 |
| DE | 102011113100 A1 | 3/2013 |
| DE | 102011116194 A1 | 4/2013 |
| DE | 102012201430 A1 | 4/2013 |
| DE | 102012216869 A1 | 3/2014 |
| DE | 202015104103 U1 | 8/2015 |
| DE | 102014002942 A1 | 9/2015 |
| DE | 102015011460 A1 | 3/2016 |
| DE | 102015011461 A1 | 3/2016 |
| DE | 102017110812 A1 | 1/2018 |
| DE | 102016011481 A1 | 3/2018 |
| DE | 202017103162 U1 | 5/2018 |
| DE | 102018000765 A1 | 8/2019 |
| DE | 102018001230 A1 | 8/2019 |
| DE | 202019100400 U1 | 1/2020 |
| DE | 202019100710 U1 | 2/2020 |
| DE | 102018007921 A1 | 4/2020 |
| DE | 202019102879 U1 | 5/2020 |
| DE | 202019105369 U1 | 5/2020 |
| DE | 102019101935 A1 * | 7/2020 ............ B60N 2/914 |
| DE | 102019008724 A1 | 8/2020 |
| EP | 1077154 A2 | 2/2001 |
| EP | 1749477 A1 | 2/2007 |
| EP | 1932715 A1 | 6/2008 |
| EP | 2149475 A1 | 2/2010 |
| EP | 2205460 B1 | 3/2016 |
| FR | 2988654 A1 | 10/2013 |
| GB | 2512136 A | 9/2014 |
| JP | 2001269380 A | 10/2001 |
| JP | 2005137896 A | 6/2005 |
| JP | 2005237456 A | 9/2005 |
| JP | 2006014756 A | 1/2006 |
| JP | 3857869 B2 | 12/2006 |
| JP | 2009172145 A | 8/2009 |
| JP | 2012196253 A | 10/2012 |
| JP | 2013163405 A | 8/2013 |
| JP | 2018095015 A | 6/2018 |
| JP | 2018130230 A | 8/2018 |
| JP | 2019131049 A | 8/2019 |
| WO | 2012/039368 | 3/2012 |
| WO | 2012039368 A1 | 3/2012 |

OTHER PUBLICATIONS

Co-Pending U.S. Appl. No. 15/930,802, filed May 13, 2020.
Co-Pending U.S. Appl. No. 15/930,835, filed May 13, 2020.
Co-Pending U.S. Appl. No. 15/930,865, filed May 13, 2020.
Co-Pending U.S. Appl. No. 17/109,652, filed Dec. 2, 2020.
German Office Action dated Oct. 4, 2022 for German Patent Application No. 10 2021 111 817.4.
Chinese Office Action dated Dec. 16, 2022 for Chinese Patent Application No. 202110511120.5.

* cited by examiner

SEAT ASSEMBLY

TECHNICAL FIELD

The present disclosure generally relates to seat assemblies, including seat assemblies that may provide guided breathing and reduced biomedical irregularities via one or more bladder assemblies.

BACKGROUND

This background description is set forth below for the purpose of providing context only. Therefore, any aspect of this background description, to the extent that it does not otherwise qualify as prior art, is neither expressly nor impliedly admitted as prior art against the instant disclosure.

Some seat assemblies may not be comfortable, may not provide sufficient functionality, may not be configured to monitor the breathing pattern of a user, and/or may not be configured to reduce irregularities in sensed biomedical information. For example and without limitation, some seat assemblies may not be configured to provide a relaxing effect to normalize/regulate breathing via one or more bladder assemblies.

There is a desire for solutions/options that minimize or eliminate one or more challenges or shortcomings of seat assemblies. The foregoing discussion is intended only to illustrate examples of the present field and is not a disavowal of scope.

SUMMARY

In embodiments, a seat assembly may include a seat, a first bladder assembly connected to the seat, a second bladder assembly connected to the seat, and/or an electrical control unit (ECU) configured to independently control the first bladder assembly and the second bladder assembly. The ECU may be configured to maintain a level of inflation of the first bladder assembly to provide a hugging effect to a user of the seat while inflating and deflating the second bladder assembly to guide breathing of said user.

With embodiments, a seat assembly may include a seat, a first bladder assembly disposed at least partially in the seat, a second bladder assembly disposed at least partially in the seat, a biomedical sensor configured to sense a breathing pattern of a user of the seat, a massage assembly including one or more massage actuators disposed at least partially in the seat, and/or an electrical control unit (ECU) connected to the biomedical sensor. The ECU may be configured to automatically and/or independently control the first bladder assembly, the second bladder assembly, and/or the massage assembly to reduce irregularities in the breathing pattern of said user.

In embodiments, a method of operating a seat assembly may include inflating one or more bladders of a first bladder assembly, maintaining a level of inflation of the one or more bladders, and/or inflating and deflating a second bladder assembly to provide a simulated breathing pattern for a user occupying the seat to reduce irregularities in a breathing pattern of said user.

The foregoing and other potential aspects, features, details, utilities, and/or advantages of examples/embodiments of the present disclosure will be apparent from reading the following description, and from reviewing the accompanying drawings.

BRIEF DESCRIPTION OF THE DRAWINGS

While the claims are not limited to a specific illustration, an appreciation of various aspects may be gained through a discussion of various examples. The drawings are not necessarily to scale, and certain features may be exaggerated or hidden to better illustrate and explain an innovative aspect of an example. Further, the exemplary illustrations described herein are not exhaustive or otherwise limiting, and are not restricted to the precise form and configuration shown in the drawings or disclosed in the following detailed description. Exemplary illustrations are described in detail by referring to the drawings as follows:

DETAILED DESCRIPTION

Reference will now be made in detail to embodiments of the present disclosure, examples of which are described herein and illustrated in the accompanying drawings. While the present disclosure will be described in conjunction with embodiments and/or examples, it will be understood that they do not limit the present disclosure to these embodiments and/or examples. On the contrary, the present disclosure covers alternatives, modifications, and equivalents.

Figure 1:
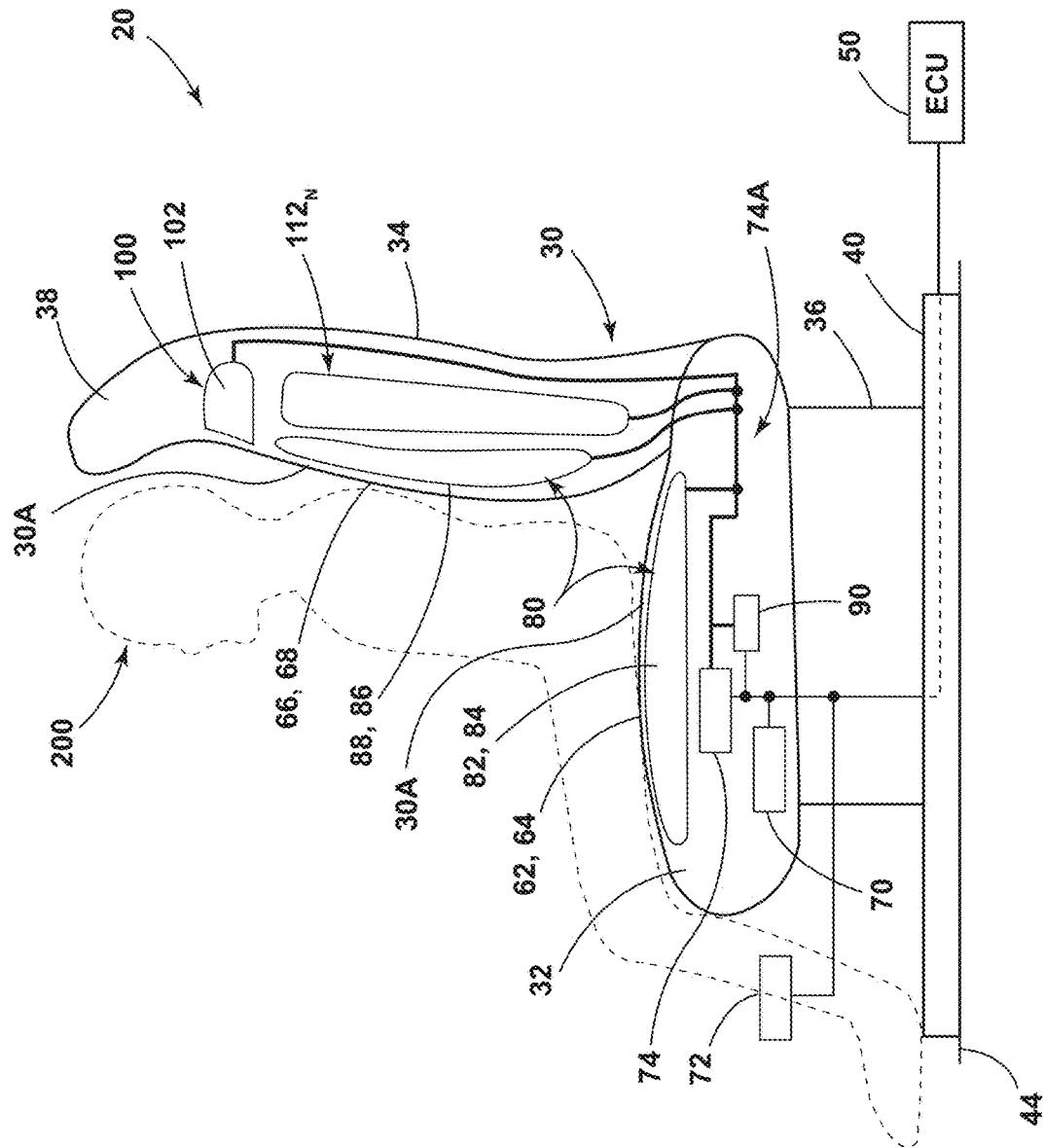
FIG. 1 is a side view generally illustrating an embodiment of a seat assembly according to teachings of the present disclosure.
Figure 2:
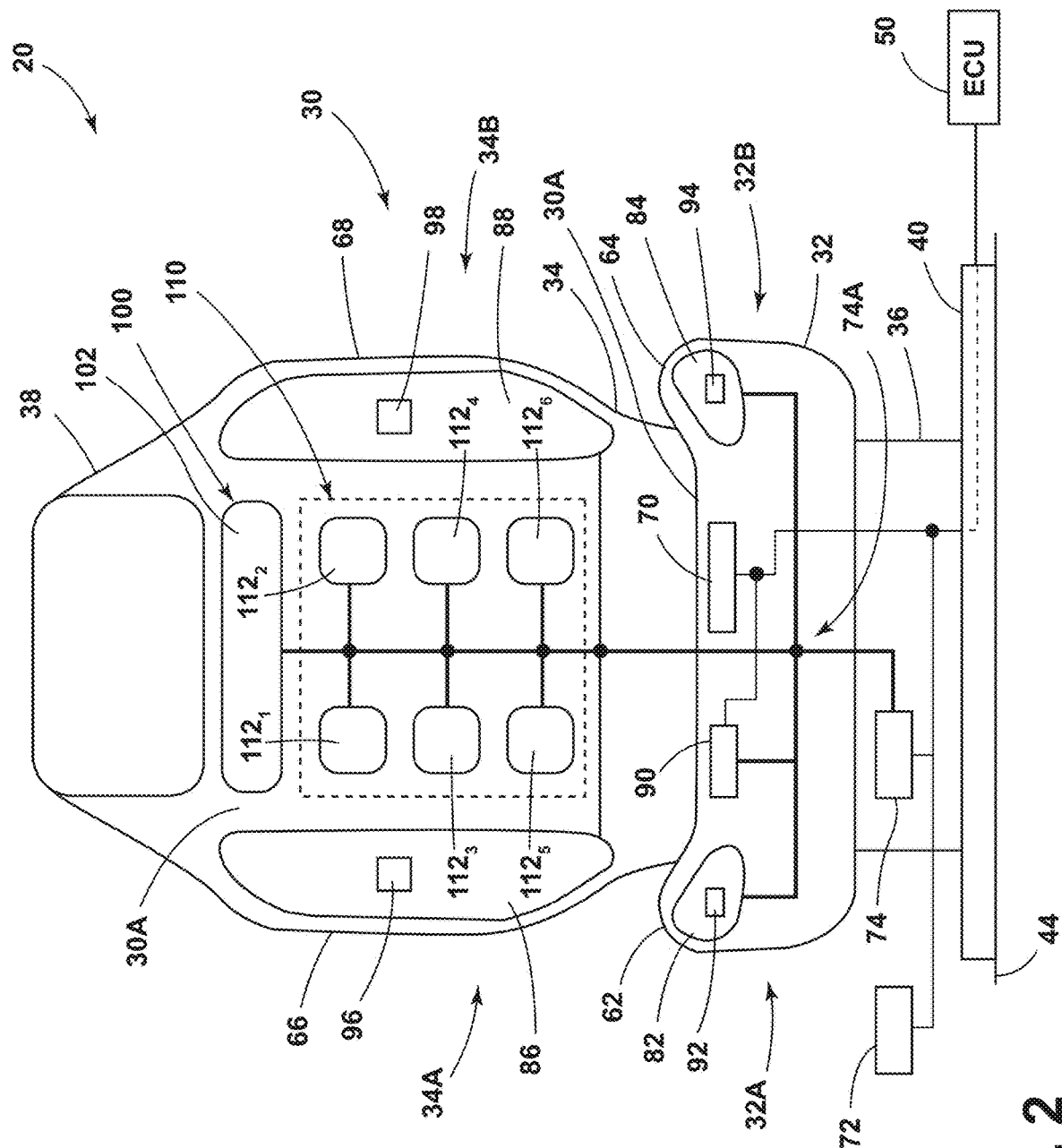
FIG. 2 is a front view generally illustrating an embodiment of a seat assembly according to teachings of the present disclosure.

In embodiments, such as generally illustrated in FIGS. 1 and 2, a seat assembly 20 may include a seat 30, an electronic control unit (ECU) 50, a first bladder assembly 80, and/or a second bladder assembly 100. The ECU 50 may be connected (e.g., electrically) with the first bladder assembly 80 and/or the second bladder assembly 100. The first bladder assembly 80 and/or the second bladder assembly 100 may be configured to provide guided breathing and/or a hugging effect to a user 200 occupying the seat 30. The ECU 50 may independently control the first bladder assembly 80 and/or the second bladder assembly 100. For example and without limitation, the ECU 50 may be configured to inflate and/or deflate the first bladder assembly 80 while inflating and/or deflating the second bladder assembly 100.

With embodiments, such as generally illustrated in FIGS. 1 and 2, a seat assembly 20 may include at least one seat 30. The seat 30 may include a seat base 32 and/or a seat back 34. The seat 30 may be selectively connected (e.g., electrically and/or mechanically) to a track assembly 40. The ECU 50 may be electrically connected to the seat 30, such as via the track assembly 40. The ECU 50 may be configured to at least partially control operation of the seat 30. The seat 30 may be connected with the track assembly 40 via a support member 36. The support member 36 may be selectively connected with the track assembly 40. For example and without limitation, the support member 36 may be configured to be inserted vertically and/or horizontally into the track assembly 40, and may be configured to be removed vertically and/or horizontally from the track assembly 40, such as in numerous positions along the track assembly 40. The support member 36 may be configured to move along the track assembly 40 (e.g., in the X-direction and/or Y-direction).

In embodiments, such as generally illustrated in FIGS. 1 and 2, the track assembly 40 may be disposed on a mounting surface 44 (e.g., a vehicle floor). The track assembly 40 may be configured to receive the seat 30 substantially in the X-direction and/or the Z-direction. The seat 30 and/or the support member 36 may be configured to be selectively inserted into and/or selectively removed from the track assembly 40 in one or more of a variety of locations along the track assembly 40. The track assembly 40 may include one or more of a variety of shapes, sizes, and/or configurations. For example and without limitation, the track assembly 40 may extend in an X-direction and/or a Y-direction such that the seat 30 may move in an X-direction and/or a Y-direction along the track assembly 40. In some embodiments, a seat 30 and/or a support member 36 may be connected to a mounting surface 44 independently of a track assembly 40 (e.g., a seat assembly 20 may not include a track assembly 40).

With embodiments, such as generally illustrated in FIGS. 1 and 2, the seat base 32 and/or seat back 34 may include one or more bolsters 62, 64, 66, 68. For example and without limitation, the seat base 32 may include a first bolster 62 and/or a second bolster 64, and/or the seat back 34 may include a third bolster 66 and/or a fourth bolster 68. The bolsters 62-68 may extend generally from sides of the seat base 32 and/or seat back 34. The bolsters 62-68 may be configured to contact one or more sides of a user 200, such as to at least partially surround the user 200. For example and without limitation, the first bolster 62 may extend along a first side 32A of the seat base 32 (e.g., in an X-direction) and/or the second bolster 64 may extend along a second side 32B of the seat base 32 (e.g., in an X-direction). The first side 32A of the seat base 32 may be opposite the second side 32B. The first bolster 62 and/or the second bolster 64 may, for example, extend upward (e.g., in a Z-direction) to a greater extent than other portions of the seat base 32, which may provide the seat base 32 with a generally U-shaped configuration. The first bolster 62 and/or the second bolster 64 may, at least in some circumstances, contact and/or abut legs (e.g., thighs) of the user 200 (e.g., in the Y-direction and/or Z-direction).

In embodiments, such as generally illustrated in FIGS. 1 and 2, a third bolster 66 and/or a fourth bolster 68 may extend along the seat back 34 (e.g., in a Z-direction when the seat back 34 is in an upright configuration). For example and without limitation, the third bolster 66 may extend from a first side 34A of the seat back 34, and/or the fourth bolster 68 may extend from a second side 34B of the seat back 34. The first side 34A of the seat back 34 may be opposite the second side 34B of the seat back 34. When the user 200 is occupying the seat 30, the third bolster 66 and/or the fourth bolster 68 may contact the shoulders, the torso, and/or the waist of the user 200, at least in some circumstances. Contact of the bolsters 66, 68 along the shoulders, the torso, and/or the waist of the user 200 may provide a relaxing/calming sensation to the user 200. A bolster 62, 64, 66, 68 may, for example and without limitation, include a generally triangular and/or ramped cross-sectional shape.

Figure 3:
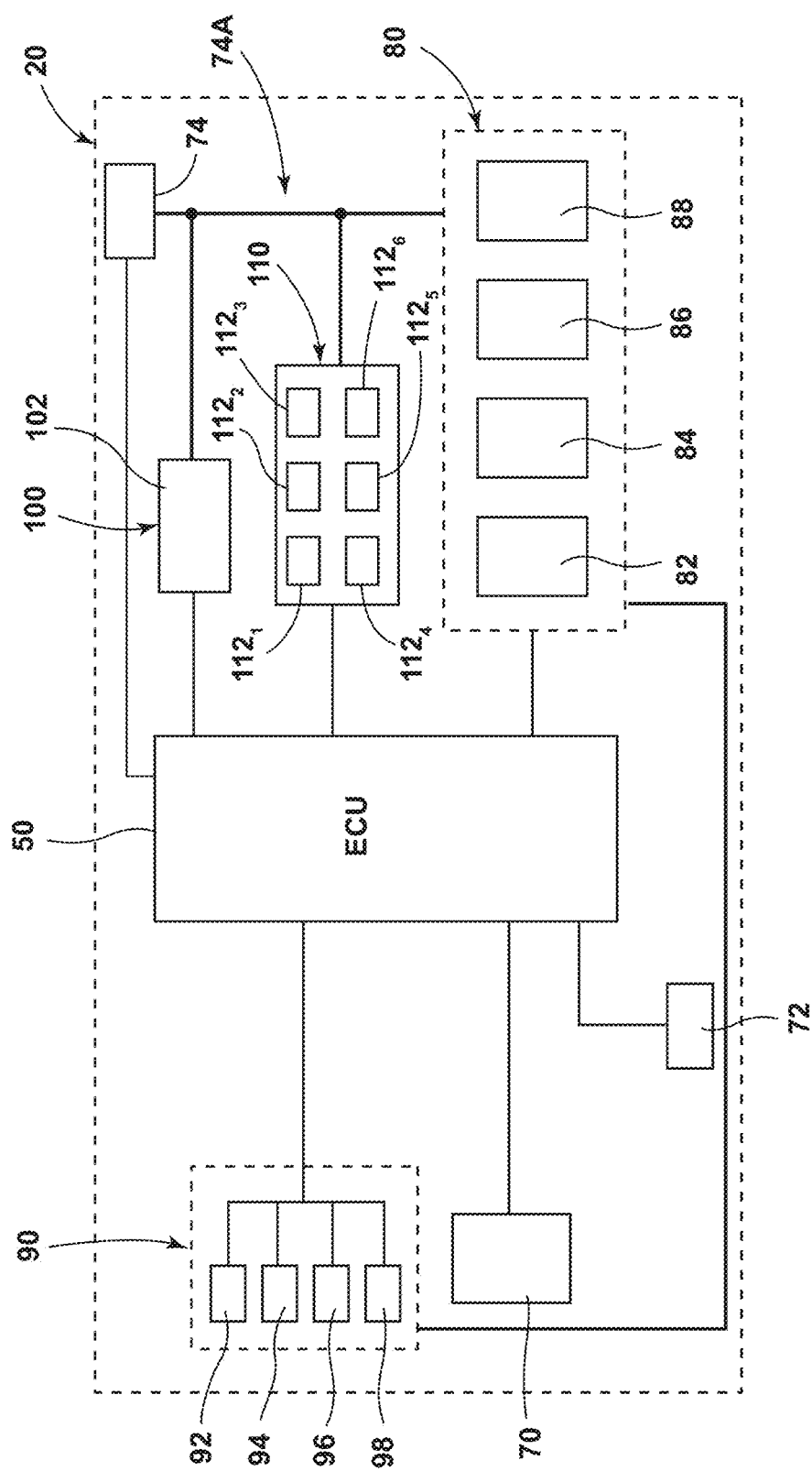
FIG. 3 is a diagram generally illustrating an embodiment of a seat assembly according to teachings of the present disclosure.

With embodiments, such as generally illustrated in FIGS. 1, 2, and 3, a seat assembly 20 may include a biomedical sensor 70. The biomedical sensor 70 may be configured to obtain/measure biomedical and/or biometric information associated with the user 200 occupying the seat 30. For example and without limitation, the biomedical sensor 70 may be configured to identify/obtain identifying information about a user 200, and/or obtain/measure a heart rate, a breathing rate, a blood pressure, and/or other health related information of the user 200. The biomedical sensor 70 may be disposed at least partially in the seat base 32 and/or the seat back 34, and/or may be disposed in another location (e.g., in a vehicle cabin). The biomedical sensor 70 may be disposed substantially proximate a seating surface 30A of the seat 30 such as to increase the accuracy of sensed biomedical information. The biomedical sensor 70 may be electrically connected (e.g., via wired and/or wireless connection) with the ECU 50. The ECU 50 may be configured to receive biomedical information from the biomedical sensor 70 and/or the ECU 50 may be configured to evaluate a state/condition of the user 200. For example and without limitation, the ECU 50 (via information sensed by the biomedical sensor 70) may be configured to determine whether the user 200 is exhibiting health irregularities (e.g., such as an irregular breathing pattern, an irregular heart rate, etc.).

With embodiments, an ECU 50 may be configured to control/activate the first bladder assembly 80 and/or the second bladder assembly 100, such as in response to sensed irregularities in biomedical information. Activating the first bladder assembly 80 and/or the second bladder assembly 100 may include inflating and/or deflating the assemblies 80, 100 to maintain one or more of a variety of levels of inflation/pressures, and/or may include inflating and/or deflating the bladder assemblies 80, 100 in a cyclical manner. For example and without limitation, the ECU 50 may activate the first bladder assembly 80 and/or the second bladder assembly 100 to reduce health irregularities (e.g., irregular breathing, irregular heart rate, irregular blood pressure, etc.).

In embodiments, the ECU 50 may determine if sensed heath irregularities have been reduced sufficiently. For example, the ECU 50 may monitor biomedical information of the user 200 (e.g., via the biomedical sensor 70), such as while the first bladder assembly 80 and/or the second bladder assembly 100 is active. If irregularities in biomedical information associated with the user 200 have been sufficiently reduced, the ECU 50 may deactivate the first bladder assembly 80 and/or the second bladder assembly 100. If the ECU 50 determines that health irregularities have not been sufficiently reduced, the ECU 50 may continue operation of the bladder assemblies 80, 100.

In embodiments, such as generally illustrated in FIGS. 1, 2, and 3, the seat assembly 20 may include a first bladder assembly 80. The first bladder assembly 80 may include one or more bladders 82, 84, 86, 88. For example and without limitation, the first bladder assembly 80 may include a first bladder 82, a second bladder 84, a third bladder 86, and/or a fourth bladder 88. The first bladder 82 may be disposed at least partially in the first bolster 62, the second bladder 84 may be disposed at least partially in the second bolster 64, the third bladder 86 may be disposed at least partially in the third bolster 66, and/or the fourth bladder 88 may be disposed at least partially in the fourth bolster 68. The first bladder assembly 80 may be connected, at least indirectly, with the ECU 50 (e.g., via a wired and/or wireless connection) such that the ECU 50 may be configured to control operation of the bladders 82-88. For example and without limitation, the ECU 50 may control a fluid source 74 to inflate and/or deflate the bladders 82-88 of the first bladder assembly 80. The fluid source 74 may, for example and without limitation, include a fluid pump, a fan, a fluid reservoir, and/or one or more control valves, among other components, that may be configured to selectively provide fluid (e.g., air) to and/or remove fluid from the bladder assemblies 80, 100. For example and without limitation, the fluid source 74 may be in fluid communication with the bladder assemblies 80, 100 via one or more fluid conduits 74A (e.g., tubes, hoses, ducts, etc.).

In embodiments, the ECU 50 may inflate and/or deflate the bladders 82-88 to increase and/or decrease the flexibility of and/or the support provided by the bolsters 62-68. Inflating the bladders 82-88 may increase the rigidity and/or decrease the flexibility of the bolsters 62-68 such that movement of the user 200 is at least partially limited (or at least more limited than prior to inflation). Deflating the bladders 82-88 may increase the flexibility and/or reduce the rigidity of the bolsters 62-68 such that the bladders 82-88 limit movement of the user 200 to a lesser degree than when inflated. The ECU 50 may maintain a level of inflation for the bladders 82-88 while the seat 30 is occupied. Maintaining a level of inflation for the bladders 82-88 (via the ECU 50) may provide the user 200 occupying the seat 30 with a hugging effect to reduce stress and/or anxiety, which may result in a decrease of irregularities associated with breathing rate, heart rate, and/or blood pressure.

With embodiments, the ECU 50 may inflate the first bladder 82 and/or the second bladder 84 such that the first bladder 82 and/or the second bladder 84 may apply pressure to, limit movement of, and/or provide increased support to lower portions of the user 200 (e.g., waist, thighs, the legs, etc.), which may provide a hugging effect to the lower portions of the user 200.

In embodiments, the ECU 50 may inflate the third bladder 86 and/or the fourth bladder 88 such that third bladder 86 and/or the fourth bladder 88 may apply pressure to, further limit movement of, and/or provide increased support to upper portions of the user 200 (e.g., torso, waist, abdomen, the shoulders, neck, etc.), which may provide a hugging effect to the upper portions of the user 200.

With embodiments, the ECU 50 may inflate the first bladder assembly 80 until the first bladder assembly 80 provides a hugging effect for the user 200, and the ECU 50 may maintain that level of inflation (e.g., to maintain the hugging effect). Providing a hugging effect, such as via maintaining the level of inflation for the bladders 82-88 within a range, may at least apply pressure and/or force to a user that may generally simulate a hug/being held or squeezed, which may generally facilitate a reduction in irregularities in biomedical information associated with the user 200 (e.g., a hug may tend to reduce stress and/or anxiety). The first bladder assembly 80 may, for example, be disposed (e.g., in bolsters 62-68) such that inflation of one or more of the bladders 82-88 applies pressure and/or force to a user 200 in a Y-direction (e.g., a transversion direction). For example and without limitation, inflating the first bladder 82 and the second bladder 84 may apply pressure and/or force to a lower portion (e.g., legs) of the user 200 in substantially opposite Y-directions (e.g., in an X-Y plane), and/or inflating the third bladder 86 and the fourth bladder 88 may apply pressure and/or force to an upper portion (e.g., torso) of the user 200 in substantially opposite Y-directions (e.g., in a Y-Z plane), which may provide a hugging (e.g., squeezing) effect for the user 200 that may simulate the feeling of receiving a hug. The ECU 50 may, for example, control a force or pressure of the hugging effect according to, at least in part, how irregular biomedical information of a user is (e.g., may increase a force or pressure if the biomedical information is more irregular/farther outside desired ranges).

In embodiments, a first bladder assembly 80 may be automatically controlled by an ECU 50 (e.g., if biomedical irregularities are sensed) and/or may be manually controlled by the user 200, such as via a user interface 72. The user interface 72 may, for example, be disposed on, in, and/or proximate the seat 30. The user interface 72 may, for example, receive commands via one or more inputs from the user 200 (e.g., audio input, motion input, physical input, etc.). The ECU 50 may be configured to control the bladders 82-88 of the first bladder assembly 80 according to input from the user 200 provided via the user interface 72.

In embodiments, such as generally illustrated in FIGS. 2 and 3, the seat assembly 20 may include a fluid sensor 90 (e.g., a fluid pressure sensor). The fluid sensor 90 may be configured to measure fluid pressures of the first bladder 82, the second bladder 84, the third bladder 86, and/or the fourth bladder 88. The fluid sensor 90 may include a first sensor portion 92, a second sensor portion 94, a third sensor portion 96, and/or a fourth sensor portion 98. The first sensor portion 92 may be disposed within and/or be connected to the first bladder 82, the second sensor portion 94 may be disposed within and/or be connected to the second bladder 84, the third sensor portion 96 may be disposed within and/or be connected to the third bladder 86, and/or the fourth sensor portion 98 may be disposed within and/or be connected to the fourth bladder 88. The sensor portions 92-98 may be configured to sense/measure pressures within the respective bladders 82-88. The fluid sensor 90 may be connected with the ECU 50 (e.g., via a wired and/or wireless connection) such that the ECU 50 may receive pressure information from the fluid sensor 90.

With embodiments, the ECU 50 may be configured to inflate and/or deflate the first bladder assembly 80 according to feedback from the fluid sensor 90 (e.g., pressure information of the first bladder 82, the second bladder 84, the third bladder 86, and/or the fourth bladder 88). The ECU 50 may be configured to maintain a level of inflation for the bladders 82-88 of the first bladder assembly 80. For example and without limitation, the ECU 50 may be configured to maintain the level of inflation of the first bladder 82, the second bladder 84, the third bladder 86, and/or the fourth bladder 88 such that the bladders 82-88 remain within a pressure range. The pressure range may correspond to a range in which the user 200 feels calmed/relaxed (e.g., when a hugging effect is provided). The ECU 50 may be configured to automatically determine an appropriate pressure range for the user 200 occupying the seat 30. For example and without limitation, the ECU 50 may determine an appropriate pressure range based on prior use, physical dimensions, and/or weight of the user 200 (which may be different for each user). The bladders 82-88 may be configured for a variety of pressure ranges. The ECU 50 may maintain the level of inflation of the first bladder assembly 80 while moving the seat base 32, the seat back 34, and/or during other seat movements, adjustments, etc.

With embodiments, while a user 200 is occupying the seat 30, the ECU 50 may inflate and/or deflate the first bladder 82, the second bladder 84, the third bladder 86, and/or the fourth bladder 88 such that the bladders 82-88 are all within appropriate pressure ranges. The ECU 50 may be configured to individually inflate and/or deflate each of the first bladder 82, the second bladder 84, the third bladder 86, and/or the fourth bladder 88. For example and without limitation, if the pressure sensed by the first sensor portion 92 is greater than a pressure range (e.g., a hugging pressure range), the ECU 50 may deflate the first bladder 82 such that the pressure of the first bladder 82 is within the pressure range. Similarly, if the pressure sensed by the second sensor portion 94 is lower than the pressure range, the ECU 50 may inflate the second bladder 84 such that the pressure of the second bladder 84 is within the pressure range.

In embodiments, such as generally illustrated in FIGS. 1, 2, and 3, a seat assembly 20 may include a second bladder assembly 100. The second bladder assembly 100 may include one or more bladders. For example and without limitation, the second bladder assembly 100 may include a fifth bladder 102. The fifth bladder 102 may be disposed at least partially in the seat back 34. For example and without limitation, the fifth bladder 102 may be disposed substantially in an upper portion of the seat back 34 (e.g., proximate a headrest 38 of the seat 30). The fifth bladder 102 may be disposed in the upper portion of the seat back 34 such that the fifth bladder 102 is proximate a neck and/or shoulders of the user 200 occupying the seat 30. The fifth bladder 102 may be connected with the ECU 50 (e.g., via a wired and/or wireless connection) and/or a fluid source 74. The ECU 50 may be configured to control operation of the second bladder assembly 100 (e.g., the fifth bladder 102), such as via the fluid source 74. The ECU 50 may inflate and/or deflate the fifth bladder 102 while independently controlling (e.g., inflating, deflating, maintaining, etc.) the first bladder assembly 80.

With embodiments, the ECU 50 may be configured to provide guided breathing to the user 200 via the second bladder assembly 100. For example and without limitation, providing guided breathing may include the ECU 50 inflating and/or deflating the fifth bladder 102 to simulate a predetermined breathing pattern. The predetermined/simulated breathing pattern may correspond to an improved, desired, and/or ideal breathing pattern for the user 200 (e.g., according to a medical history of the user, medical standards, advice/information from a medical professional, etc.). The guiding effects of the second bladder assembly 100 may generally cause a user 200 of the seat 30 to gradually modify their breathing such that the breathing pattern of the user 200 may gradually move toward mirroring the simulated breathing pattern (e.g., the simulated breathing pattern may decrease the irregularities in the breathing pattern of the user 200 as the user 200 breathes in a pattern generally matching the fifth bladder 102). The ECU 50 may automatically control the fifth bladder 102 to provide guided breathing if an irregular breathing pattern is sensed (e.g., via a biomedical sensor 70). Additionally or alternatively, the user 200 may manually activate the second bladder assembly 100 and/or guided breathing via the user interface 72, which may be connected with the ECU 50 and/or the second bladder assembly 100.

In embodiments, such as generally illustrated in FIGS. 1, 2, and 3, a seat assembly 20 may include a massage assembly 110. The massage assembly 110 may be disposed in the seat base 32 and/or the seat back 34. For example and without limitation, the massage assembly 110 may be disposed in a middle portion of the seat back 34 (see, e.g., FIG. 2). The massage assembly 110 may, for example, include one or massage actuators $112_N$. For example and without limitation, the massage assembly 110 may include a first massage actuator $112_1$, a second massage actuator $112_2$, a third massage actuator $112_3$, a fourth massage actuator $112_4$, a fifth massage actuator $112_5$, and/or a sixth massage actuator $112_6$. One or more of the massage actuators $112_N$ may be disposed in the seat back 34, such as substantially proximate a shoulder area, a thoracic area, and/or a lumbar area of the user 200. For example and without limitation, the first massage actuator $112_1$, the third massage actuator $112_3$, and/or the fifth massage actuator $112_5$ may be disposed proximate a first side 34A of the seat back 34. Additionally or alternatively, the second massage actuator $112_2$, the fourth massage actuator $112_4$, and/or the sixth massage actuator $112_6$ may be disposed proximate the second side 34B of the seat back 34. A massage actuator $112_N$ may, for example and without limitation, include a fluid bladder and/or an eccentric electric motor.

With embodiments, the massage assembly 110 may be connected (e.g., via wired and/or wireless connection) with the ECU 50 such that the ECU 50 may individually control each massage actuator $112_N$ of the massage assembly 110. For example and without limitation, if the massage actuators $112_N$ include fluid bladders, the ECU 50 may be configured to inflate and/or deflate the first massage actuator $112_1$, the second massage actuator $112_2$, the third massage actuator $112_3$, the fourth massage actuator $112_4$, the fifth massage actuator $112_5$, and/or the sixth massage actuator $112_6$ to increase and/or decrease the pressure applied to one or more of a variety of portions of the back of the user 200, which may provide a massaging effect. The massage actuators $112_N$ may be connected to (e.g., in fluid communication with) a fluid source 74, and/or the ECU 50 may control the fluid source 74 to inflate and deflate the massage actuators $112_N$.

In embodiments, the massage actuators $112_N$ may be configured to apply one or more of a variety of pressures/forces to the user 200. For example and without limitation, the ECU 50 may be configured to activate the massage actuators $112_N$ to provide a first level of intensity (e.g., a low/introduction level of intensity), a second level of intensity (e.g., to warm up tissues of the user 200), and/or a third level of intensity (e.g., to relax tension in medium and deep muscle layers and/or release restrictions in connective tissues). The first level of intensity may apply less pressure/force to the user 200 than the second level of intensity and/or the third level of intensity. The third level of intensity may apply more pressure/force to the user 200 than the first level of intensity and/or the second level of intensity. The ECU 50 may automatically activate the massage assembly 110, such as if irregular biomedical information is sensed via the biomedical sensor 70. Additionally or alternatively, the user 200 may manually activate and/or control operation of the massage assembly 110 via a user interface 72, which may be connected with the ECU 50 and/or the massage assembly 110.

Figure 4:
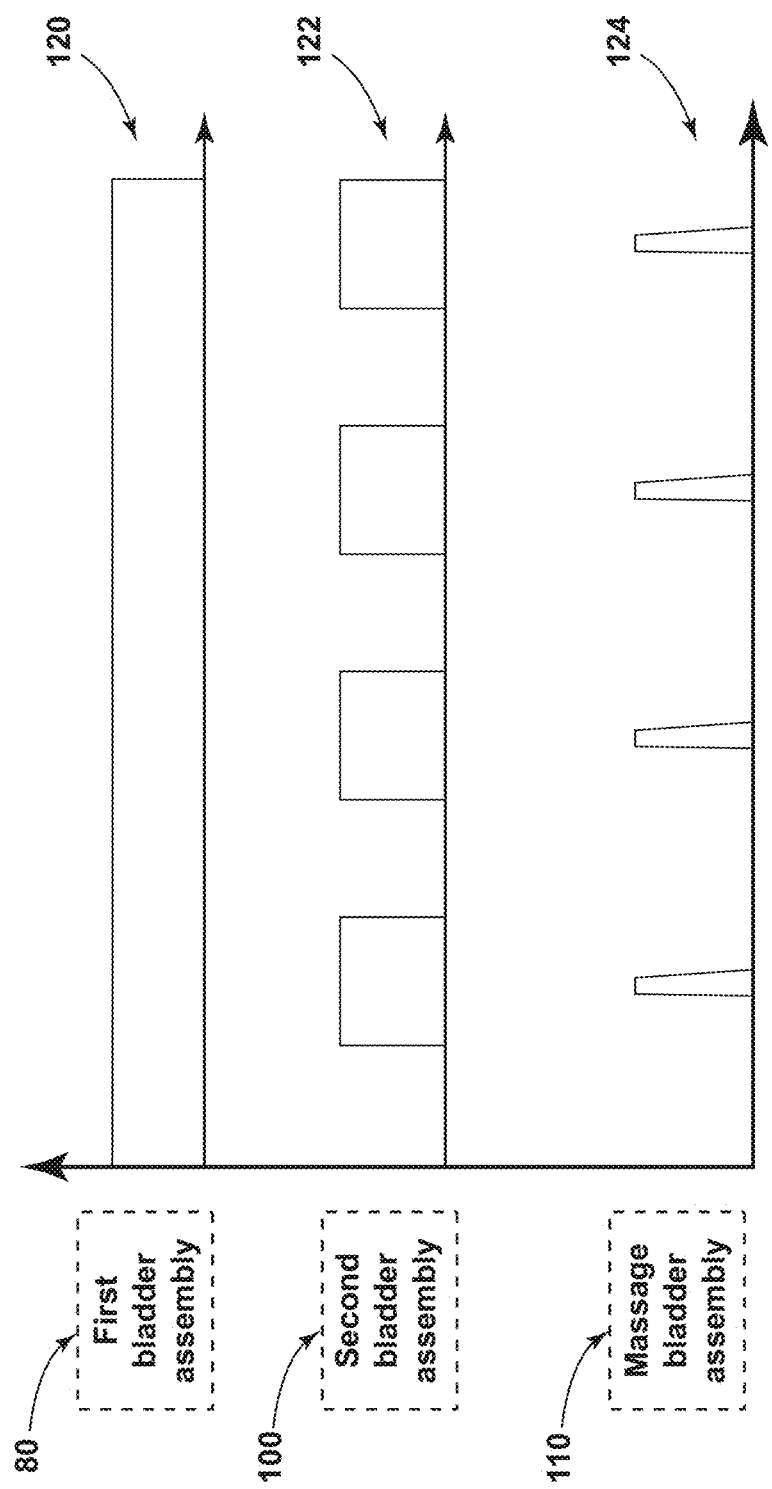
FIG. 4 is a graph generally illustrating portions of an embodiment of a method of operating a seat assembly according to teachings of the present disclosure.
Figure 5:
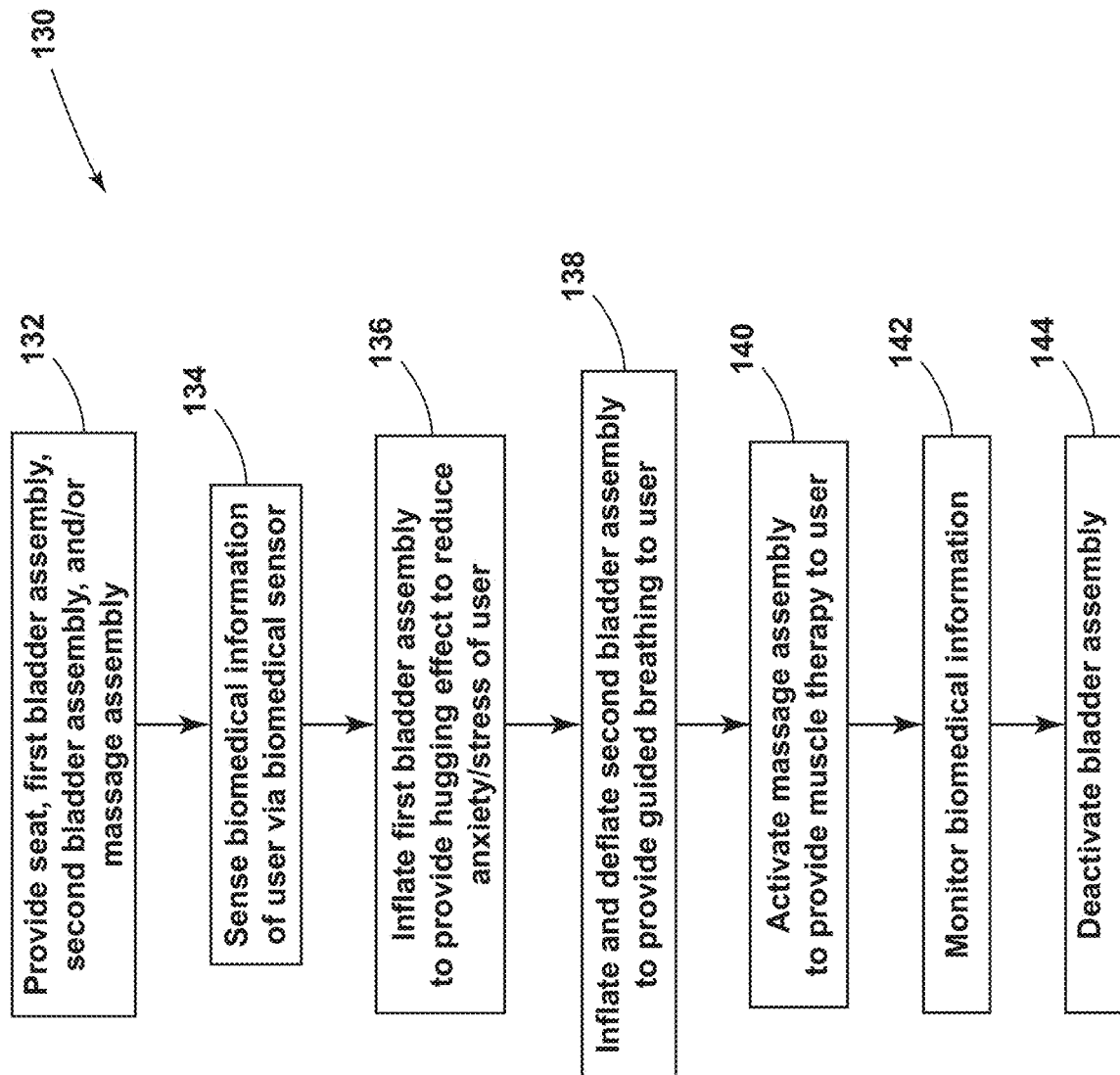
FIG. 5 is a flowchart generally illustrating an embodiment of a method of operating a seat assembly according to teachings of the present disclosure.

In embodiments, such as generally illustrated in FIGS. 4 and 5, a method 130 of operating a seat assembly 20 may include providing a seat 30, a first bladder assembly 80, a second bladder assembly 100, a massage assembly 110, and/or an ECU 50 (step 132). The seat assembly 20 may include a biomedical sensor 70 and/or a fluid sensor 90 connected with the ECU 50. The method 130 may include sensing biomedical information of the user 200 occupying the seat 30 (step 134). Sensing biomedical information may include identifying the user 200 (e.g., biomedical information may include biometric information) and/or determining a breathing pattern, breathing rate, heart rate, and/or blood pressure of the user 200. If the ECU 50 senses, via the biomedical sensor 70, that the user 200 has irregular and/or undesired biomedical information, the ECU 50 may activate the first bladder assembly 80 (see, e.g., first bladder assembly plot 120). The ECU 50 may activate the first bladder assembly 80 to reduce irregularities in the biomedical information of the user (step 136). Activating the first bladder assembly 80 may include inflating the bladders 82-88 and maintaining a level of inflation of the first bladder assembly 80 to provide a hugging effect for the user 200, which may reduce anxiety, stress, and/or normalize biomedical information. The ECU 50 may maintain a level of inflation of the first bladder assembly 80 while continuing to sense biomedical information of the user 200.

With embodiments, the method 130 may include providing guided breathing to the user 200 via the second bladder assembly 100 while the first bladder assembly 80 is inflated/maintained (step 138) (see, e.g., second bladder assembly plot 122). The ECU 50 may inflate and/or deflate the second bladder assembly 100 (e.g., a fifth bladder 102) while maintaining a level of inflation of the one or more bladders 82-88 of the first bladder assembly 80. As the fifth bladder 102 inflates and/or deflates, the breathing pattern of the user 200 may at least start to mirror the simulated breathing pattern created by the fifth bladder 102. Additionally or alternatively, the ECU 50 may activate (e.g., periodically) the massage assembly 110 (step 140), such as while the first bladder assembly 80 and/or the second bladder assembly 100 are inflated and/or deflated. For example, massage assembly plot 124 reflects an example of a massage assembly 110 periodically in an active/high state (e.g., massaging) and an inactive/low state (e.g., not massaging). The ECU 50 may provide a hugging/relaxing effect via the first bladder assembly 80, provide guided breathing via the second bladder assembly 100, and/or massage the user 200 via the massage assembly 110 at the same time, such as to reduce irregularities in the biomedical information (e.g., a breathing pattern) of the user 200 (see, e.g., FIG. 4).

With embodiments, the ECU 50 may monitor (e.g., continuously) the biomedical information of the user 200, such as via the biomedical sensor 70 (step 142). If the ECU 50 determines that irregularities in the biomedical information of a user 200 have been sufficiently reduced (e.g., are below or within an acceptable threshold), the ECU 50 may deactivate the first bladder assembly 80, the second bladder assembly 100, and/or the massage assembly 110 (step 144).

In examples, an ECU (e.g., ECU 50) may include an electronic controller and/or include an electronic processor, such as a programmable microprocessor and/or microcontroller. In embodiments, an ECU may include, for example, an application specific integrated circuit (ASIC). An ECU may include a central processing unit (CPU), a memory (e.g., a non-transitory computer-readable storage medium), and/or an input/output (I/O) interface. An ECU may be configured to perform various functions, including those described in greater detail herein, with appropriate programming instructions and/or code embodied in software, hardware, and/or other medium. In embodiments, an ECU may include a plurality of controllers. In embodiments, an ECU may be connected to a display, such as a touchscreen display.

Various examples/embodiments are described herein for various apparatuses, systems, and/or methods. Numerous specific details are set forth to provide a thorough understanding of the overall structure, function, manufacture, and use of the examples/embodiments as described in the specification and illustrated in the accompanying drawings. It will be understood by those skilled in the art, however, that the examples/embodiments may be practiced without such specific details. In other instances, well-known operations, components, and elements have not been described in detail so as not to obscure the examples/embodiments described in the specification. Those of ordinary skill in the art will understand that the examples/embodiments described and illustrated herein are non-limiting examples, and thus it can be appreciated that the specific structural and functional details disclosed herein may be representative and do not necessarily limit the scope of the embodiments.

Reference throughout the specification to "examples, "in examples," "with examples," "various embodiments," "with embodiments," "in embodiments," or "an embodiment," or the like, means that a particular feature, structure, or characteristic described in connection with the example/embodiment is included in at least one embodiment. Thus, appearances of the phrases "examples, "in examples," "with examples," "in various embodiments," "with embodiments," "in embodiments," or "an embodiment," or the like, in places throughout the specification are not necessarily all referring to the same embodiment. Furthermore, the particular features, structures, or characteristics may be combined in any suitable manner in one or more examples/embodiments. Thus, the particular features, structures, or characteristics illustrated or described in connection with one embodiment/example may be combined, in whole or in part, with the features, structures, functions, and/or characteristics of one or more other embodiments/examples without limitation given that such combination is not illogical or non-functional. Moreover, many modifications may be made to adapt a particular situation or material to the teachings of the present disclosure without departing from the scope thereof.

It should be understood that references to a single element are not necessarily so limited and may include one or more of such element. Any directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of examples/embodiments.

Joinder references (e.g., attached, coupled, connected, and the like) are to be construed broadly and may include intermediate members between a connection of elements and relative movement between elements. As such, joinder references do not necessarily imply that two elements are directly connected/coupled and in fixed relation to each other. The use of "e.g." in the specification is to be construed broadly and is used to provide non-limiting examples of embodiments of the disclosure, and the disclosure is not limited to such examples. Uses of "and" and "or" are to be construed broadly (e.g., to be treated as "and/or"). For example and without limitation, uses of "and" do not necessarily require all elements or features listed, and uses of "or" are inclusive unless such a construction would be illogical.

While processes, systems, and methods may be described herein in connection with one or more steps in a particular sequence, it should be understood that such methods may be practiced with the steps in a different order, with certain steps performed simultaneously, with additional steps, and/or with certain described steps omitted.

All matter contained in the above description or shown in the accompanying drawings shall be interpreted as illustrative only and not limiting. Changes in detail or structure may be made without departing from the present disclosure.

It should be understood that an electronic control unit (ECU), a system, and/or a processor as described herein may include a conventional processing apparatus known in the art, which may be capable of executing preprogrammed instructions stored in an associated memory, all performing in accordance with the functionality described herein. To the extent that the methods described herein are embodied in software, the resulting software can be stored in an associated memory and can also constitute means for performing such methods. Such a system or processor may further be of the type having ROM, RAM, RAM and ROM, and/or a combination of non-volatile and volatile memory so that any software may be stored and yet allow storage and processing of dynamically produced data and/or signals.

It should be further understood that an article of manufacture in accordance with this disclosure may include a non-transitory computer-readable storage medium having a computer program encoded thereon for implementing logic and other functionality described herein. The computer program may include code to perform one or more of the methods disclosed herein. Such embodiments may be configured to execute via one or more processors, such as multiple processors that are integrated into a single system or are distributed over and connected together through a communications network, and the communications network may be wired and/or wireless. Code for implementing one or more of the features described in connection with one or more embodiments may, when executed by a processor, cause a plurality of transistors to change from a first state to a second state. A specific pattern of change (e.g., which transistors change state and which transistors do not), may be dictated, at least partially, by the logic and/or code.

What is claimed is:

1. A seat assembly, including:
   a seat;
   a first bladder assembly connected to the seat;
   a second bladder assembly connected to the seat;
   an electrical control unit (ECU) configured to independently control the first bladder assembly and the second bladder assembly; and
   a biomedical sensor connected with the ECU;
   wherein the ECU is configured to adjust or maintain a level of inflation of the first bladder assembly to provide a hugging effect to a user of the seat while inflating and deflating the second bladder assembly to guide breathing of said user;
   the ECU is configured to sense a breathing pattern of said user via the biomedical sensor;
   the ECU is configured to determine if the breathing pattern is irregular; and
   if the breathing pattern is irregular, the ECU is configured to automatically activate the first bladder assembly and the second bladder assembly to reduce irregularities in the breathing pattern of said user.

2. The seat assembly of claim 1, wherein the second bladder assembly is disposed to substantially align with a neck and/or shoulders of said user.

3. The seat assembly of claim 1, including a fluid source in fluid communication with the first bladder assembly and the second bladder assembly;
   wherein the ECU is configured to control the fluid source to inflate and deflate the first bladder assembly and the second bladder assembly.

4. The seat assembly of claim 3, wherein the fluid source includes a fluid pump.

5. The seat assembly of claim 1, wherein the seat includes one or more bolsters, and a bladder of the first bladder assembly is disposed in at least one of the one or more bolsters.

6. The seat assembly of claim 1, wherein the seat includes a seat base and a seat back;
   the seat base includes a first bolster and a second bolster;
   the seat back includes a third bolster and a fourth bolster;
   the first bladder assembly includes a first bladder, a second bladder, a third bladder, and a fourth bladder;
   the first bladder and the second bladder are disposed at least partially in the first bolster and the second bolster, respectively; and
   the third bladder and the fourth bladder are disposed at least partially in the third bolster and the fourth bolster, respectively.

7. The seat assembly of claim 6, wherein the ECU is configured to maintain the level of inflation for the first bladder, the second bladder, the third bladder, and the fourth bladder of the first bladder assembly to provide the hugging effect while guiding breathing of the user via the second bladder assembly.

8. The seat assembly of claim 6, including a fluid pressure sensor having a first sensor portion, a second sensor portion, a third sensor portion, and a fourth sensor portion;
   wherein the first sensor portion is configured to sense a pressure of the first bladder;
   the second sensor portion is configured to sense a pressure of the second bladder;
   the third sensor portion is configured to sense a pressure of the third bladder;
   the fourth sensor portion is configured to sense a pressure of the fourth bladder; and
   maintaining the level of inflation includes inflating and deflating the first bladder, the second bladder, the third bladder, and/or the fourth bladder such that each of the first bladder, the second bladder, the third bladder, and the fourth bladder are within a pressure range.

9. The seat assembly of claim 1, including a massage assembly connected to the seat;
   wherein the massage assembly is connected with the ECU; and
   the ECU is configured to automatically activate the massage assembly to massage said user to reduce irregularities in the breathing pattern of said user while (i) adjusting or maintaining the level of inflation of the first bladder assembly to provide the hugging effect, and (ii) inflating and deflating the second bladder assembly to guide breathing.

10. The seat assembly of claim 9, wherein the massage assembly includes one or more massage bladders; and
    the ECU is configured to inflate and deflate the one or more massage bladders to massage said user to reduce irregularities in the breathing pattern of said user.

11. The seat assembly of claim 10, wherein the ECU is configured to control a fluid source connected to the first bladder assembly, the second bladder assembly, and the one or more massage bladders.

12. A seat assembly, including:
    a seat;
    a first bladder assembly disposed at least partially in the seat;
    a second bladder assembly disposed at least partially in the seat;
    a biomedical sensor configured to sense a breathing pattern of a user of the seat;
    a massage assembly including one or more massage actuators disposed at least partially in the seat; and
    an electrical control unit (ECU) connected to the biomedical sensor;
    wherein the ECU is configured to:
    automatically and independently control the first bladder assembly, the second bladder assembly, and the massage assembly to reduce irregularities in the breathing pattern of said user;
    determine if the breathing pattern sensed via the biomedical sensor is irregular; and automatically activate the first bladder assembly and to maintain a level of inflation of the first bladder assembly to provide a hugging effect to said user when the breathing pattern is irregular.

13. The seat assembly of claim 12, where the ECU is configured to maintain the level of inflation of the first bladder assembly to provide the hugging effect while inflating and deflating the second bladder assembly to provide a guided breathing pattern for said user.

14. A method of operating a seat assembly including a seat, a first bladder assembly, and a second bladder assembly, the method including:
  sensing a breathing pattern of a user occupying the seat via a biomedical sensor;
  determining if the breathing pattern of said user includes irregularities via an electronic control unit (ECU);
  inflating one or more bladders of the first bladder assembly;
  maintaining a level of inflation of the one or more bladders; and
  inflating and deflating the second bladder assembly to provide a simulated breathing pattern for said user to reduce irregularities in the breathing pattern of said user.

15. The method of claim 14, wherein inflating and deflating the second bladder assembly includes the ECU automatically controlling a fluid source to inflate and deflate the second bladder assembly while controlling the fluid source to maintain the level of inflation of the one or more bladders of the first bladder assembly.

16. The method of claim 14, including:
  wherein inflating the first bladder assembly includes automatically inflating the first bladder assembly if the breathing pattern is irregular; and
  inflating and deflating the second bladder assembly includes automatically inflating and deflating the second bladder assembly if the breathing pattern is irregular.

17. The method of claim 14, including inflating and deflating one or more massage bladders of a massage assembly to prove a massaging effect to said user to reduce irregularities in the breathing pattern of said user.

18. The method of claim 17, including deactivating the first bladder assembly, the second bladder assembly, and/or the massage assembly when irregularities of the breathing pattern have been reduced below a threshold.

* * * * *